US012409059B2

(12) United States Patent
Lee

(10) Patent No.: US 12,409,059 B2
(45) Date of Patent: Sep. 9, 2025

(54) ABDOMINAL BRACING AND POSTURE CORRECTION METHOD AND TRAINING DEVICE

(71) Applicant: Linton Lee, Windsor (CA)

(72) Inventor: Linton Lee, Windsor (CA)

( * ) Notice: Subject to any disclaimer, the term of this patent is extended or adjusted under 35 U.S.C. 154(b) by 381 days.

(21) Appl. No.: 17/810,993

(22) Filed: Jul. 6, 2022

(65) Prior Publication Data

US 2024/0009017 A1    Jan. 11, 2024

(51) Int. Cl.
*A61F 5/02*    (2006.01)

(52) U.S. Cl.
CPC .................................. *A61F 5/026* (2013.01)

(58) Field of Classification Search
CPC .. A61F 5/03; A61F 5/026; A61F 5/022; A61F 5/028; A61F 5/28; A61F 5/30; A61F 5/0193; A61F 5/24; A61F 5/26; A61F 5/449; A61F 7/02; A61F 2005/0183; A61F 2007/023; A61F 2007/0096; A61F 2007/0023; A61F 13/148; A61F 13/143; A41C 1/10; A41D 1/21; A41D 13/0525; A41D 13/1236; A44B 11/28
USPC ..... 128/96, 99.1, 104.1, 109.1, 121.1, 116.1, 128/122.1, 124.1, 108.1, 105.1; 602/19
See application file for complete search history.

(56) References Cited

U.S. PATENT DOCUMENTS

| | | | | | |
|---|---|---|---|---|---|
| 899,828 | A | * | 9/1908 | Ozarnkowsky | ......... A41F 11/16 2/314 |
| 1,606,214 | A | * | 11/1926 | Ferron | ...................... A61F 5/24 128/115.1 |
| 5,823,913 | A | * | 10/1998 | Aruin | ................. A63B 23/0244 482/148 |
| 6,129,691 | A | * | 10/2000 | Ruppert | ................. A61F 5/026 128/845 |
| 2009/0192425 | A1 | * | 7/2009 | Garth | ...................... A61F 5/028 602/19 |
| 2015/0173932 | A1 | * | 6/2015 | Harcke, Jr. | ............. A61F 5/058 602/19 |

FOREIGN PATENT DOCUMENTS

AT            504271 A2 *  4/2008

* cited by examiner

*Primary Examiner* — Alireza Nia
*Assistant Examiner* — Michael Milo

(57) ABSTRACT

The current invention is a method intended to cause abdominal bracing and improve pelvic, neck and back posture by providing focus on a specific area of the abdominal muscles at the front of the body and not on the sides, back muscles or spine of the user. Continued, deep inward pressure is applied to a small area on the relaxed rectus abdominis muscle at a specific point. The user contracts only the small area of the rectus abdominis receiving the inward pressure to push outward against the pressure; this causes abdominal bracing and causes the user's anterior and posterior torso and neck muscles to correct the user's pelvic, back, shoulder and neck posture. The continued inward pressure described in the method may be applied by a specialized belt capable of applying continuous, deep inward pressure to a single small area only on the front of the abdomen.

4 Claims, 4 Drawing Sheets

ABDOMINAL BRACING AND POSTURE CORRECTION METHOD AND TRAINING DEVICE

SUMMARY OF THE INVENTION

The current invention is a method intended to cause abdominal bracing and improve pelvic, neck and back posture by providing focus on a specific area of the abdominal muscles at the front of the body and not on the sides, back muscles or spine of the user. The method begins with locating a mid-sagittal (midline) point (along the linea alba) on the rectus abdominis muscle, inferior to the umbilicus (navel) where deep inward pressure is applied to a small area of the relaxed muscle. The user continues to apply inward pressure directly to the point mentioned above to maintain constant low to moderate muscle recruitment and activation, specifically in the lower rectus abdominis region between the umbilicus and the pubic symphysis and crest (only the small area of the rectus abdominis receiving the inward pressure is contracted to push outward against the continued inward pressure); this causes abdominal bracing to stabilize the vertebral column and balance opposing forces from the lower back musculature during both static postures and dynamic movement patterns. The flexion forces coming from the anterior abdominal muscles tilt the anterior pelvis upward in order to control the relative movement that is or would be produced by concurrent forces from the posterior lower back muscles pulling the back of the pelvis upwards causing the user's anterior and posterior torso and neck muscles to correct the user's pelvic, back, shoulder and neck posture. Continued inward pressure described in the method may be applied by an external device, such as a specialized belt, capable of applying deep inward pressure to a single small area only on the front of the abdomen.

TECHNICAL FIELD OF THE INVENTION

The present invention relates generally to pressure point devices and in particular one that initiates abdominal bracing and improves posture in the lower torso, upper torso and neck while in standing, sitting and prone positions.

The invention described herein relates generally to stabilization of the spine and correct posture. In particular, the invention is directed to a method and device which, with correct use: (1) causes the wearer to stabilize their spine through abdominal bracing; (2) causes the wearer's torso and neck muscles to automatically adopt good pelvic, spinal and shoulder posture.

PRIOR ART

U.S. Pat. No. 6,645,128 to Kyung Man Hur. The invention relates to an improved exercise belt with compressible hemispherical protruding elements at the inside front of the belt that apply localized pressure to and massage the abdomen of the user as well as massaging elements along the sides of the belt. As shown in the available figures in the patent papers, the front panels which overlay the abdomen of the wearer covers a significant portion of the wearer's lower abdomen as do the foam pads contacting the sides of the wearer. The purpose of the invention seems to be to provide massage and stimulation to the sides and abdomen of the wearer during exercise and does not provide any focus on back posture. The overall belt width applies pressure all around the user's abdomen which will not cause any automatic posture correction. This design is not able to provide a single small area of localized inward pressure on the front of the abdomen.

U.S. Pat. No. 10,736,766 to Lori Booker. The invention relates to a belt with inflatable air bladders on the rear panel of the belt to support the back and mechanically improve back posture by moving, supporting and holding muscles in a configuration of good posture.

US20100076358A1—Carolyn Anne Richardson. The invention relates to a belt which provides feedback to the wearer that their abdominal hollowing (actively pulling the abdominal muscles inward towards the spine) is failing and the wearer needs to actively reproduce their abdominal hollowing. The feedback to the wearer is due to a lower back pad which will push on the wearers lower back if they cease to actively pull their abdominal muscles in toward their spine (essentially make their abdomens thinner). There is an umbilical pad on the front which may have ridges and may be intended to provide some discomfort as a reminder when the pad is held too tightly against the umbilical area if the abdominal hollowing is released. The umbilical pad is stated as 9 cm×9 cm and 1.5 cm deep. This large surface area and small depth of umbilical pad is incapable of providing a single point of small, localized deep inward mid-sagittal pressure on the rectus abdominis, inferior of the umbilicus, as required by the novel method of abdominal bracing and posture correction described herein.

The previous art in the field of back posture improvement focuses on the support of the back and the muscles of the back. The previous art in the field of exercise belts which provide localized pressure on the abdomen of the wearer, provide pressure in multiple areas of the front, back and sides of the abdominal area which cause the wearer to contract lower abdominal muscles in an attempt to pull them away from the multiple points of pressure which may adversely affect back posture.

Abdominal bracing, as first described in Low Back Disorders: Evidence Based Prevention and Rehabilitation (McGill, 2007. Human Kinetics Publishers), stabilizes the spine as the muscles surrounding the spine are contracted. Currently known abdominal bracing methods require the individual to correctly position their pelvis and back (i.e. good posture) before beginning abdominal bracing. Current abdominal bracing methods only ensure that the spine is stabilized and supported in whatever posture it was in when the bracing began.

Abdominal bracing is known to experts in the fields of physiotherapy, occupational therapy, chiropractic, sports medicine/training and core stability/posture research. In addition, abdominal bracing and methods to perform the maneuver are known to some athletes, most of them at the very highest of skill levels. One of the goals of abdominal bracing used by physiotherapists, chiropractors and researchers is for the individual to be able to hold an 8%-10% contraction of all abdominal bracing muscles all the time so that the spine is supported and protected all the time. An additional goal is to have the individual vary their abdominal bracing muscle contraction levels to match their changing levels of physical activity and exertion.

Abdominal bracing is difficult to describe and teach. The abdomen can be thought of as a cylindrical canister with the body of the canister being the muscles enclosing the abdomen, the top being the diaphragm muscle, and the bottom being the pelvic floor muscles. All these muscles in contraction will form a strong canister unit. Contracting all these muscles with equal effort and all at the same time is abdominal bracing. Maintaining abdominal bracing muscle contraction as a constant and also varying the level of bracing muscle contraction requires high levels of skill and mental effort.

Posture correction techniques are known to persons in the fields of physiotherapy, occupational therapy, chiropractic, sports medicine/training and core stability/posture research, but not limited to experts and those who are highly skilled. Correct posture explanations and methods are ubiquitous. Typical posture correction instructions for the pelvis, lower back, upper back, shoulders and neck are, nevertheless, difficult to describe to an individual and consist of many steps that the individual needs to follow in order to achieve corrected posture.

There is neither a simple explanation nor simple method for abdominal bracing, but abdominal bracing is well known to experts. There is no simple method for correcting total posture, only separate instructions for correcting parts of good posture such as hips/pelvis, lower back, upper back, shoulders and neck. The intersection of abdominal bracing and posture correction is devoid of any known cause and effect connections between the two fields.

The current invention is a method of abdominal bracing which causes posture correction, and is a new invention which has no basis in any currently described methods of abdominal bracing or posture correction.

BRIEF DESCRIPTION OF FIGURES

The scope of the invention is not limited by the form illustrated in the drawings.

DETAILED DESCRIPTION OF THE INVENTION

The primary muscle actively contracted by the individual when using the new method of abdominal bracing and posture correction described herein is the rectus abdominis. Abdominal bracing muscles which are synergistically co-activated when using the new method are Rectus Abdominis, Internal and External Obliques, Transverse Abdominis, Spinal Erectors, Deep Hip Flexors, Gluteal, Pelvic floor muscles and the Diaphragm. The lower back muscles such as the erector spinae, multifidi and quadratus lumborum are activated to balance the forces and maintain a neutral lordotic curve of the lumbosacral region, avoiding excessive anterior or posterior pelvic tilt, in conjunction with the abdominal muscles mentioned above. The aforementioned muscles are known to be actively contracted using traditional abdominal bracing techniques known prior to the current invention.

Additional muscles synergistically co-activated are the Latissimus Dorsi, Trapezius, Rhomboids, Pectorals, Sternocleidomastoid, deep neck muscles, and additional muscles controlling the anterior of the shoulder. These muscles are not used in current abdominal bracing, and are responsible for the upper body posture correction that the individual experiences when using the new method.

The only muscle area actively contracted by the individual is the small area of the rectus abdominis which is pushing against the deep inward pressure as described in the new method. All other (abdominal bracing and postural) muscles involved in the new method except for the one small active area of the rectus abdominis are synergistically co-activated. Using the new method, there is constant abdominal bracing which allows for a natural balance to occur between antagonistic pairs of muscles on the anterior and posterior of the individual's torso and neck which pull the pelvis, spine and neck into a neutral and corrected posture. This natural balance of antagonistic pairs of muscles occurs because the individual is only concentrating effort to actively contract and control a single small area on the rectus abdominis.

The new method of abdominal bracing allows the individual to maintain a constant, low level (8%-10%) of abdominal bracing muscle contraction with little active muscle contraction effort or mental effort. The new method of constant abdominal bracing allows the individual to easily increase the level of abdominal bracing through a stronger contraction of the small area of the rectus abdominis muscle as physical activity and exertion is increased.

Figure 1:
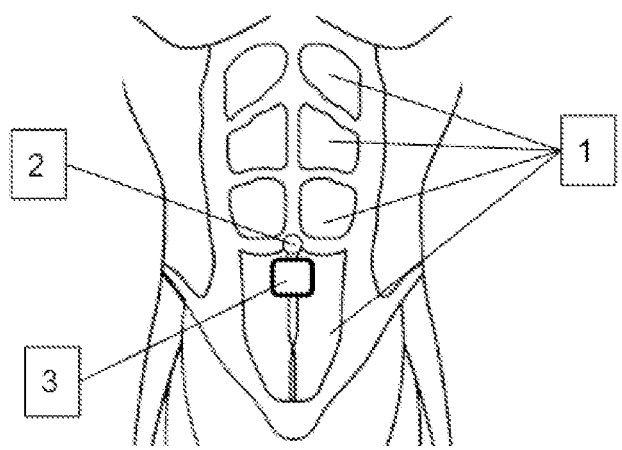
FIG. 1.—shows a front view of the human abdominal musculature
Figure 2:
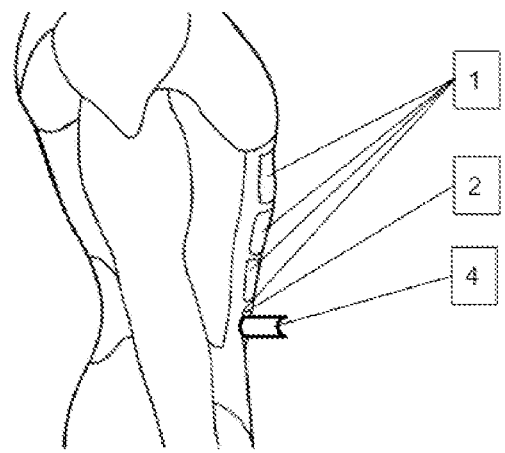
FIG. 2.—shows a side view of the human abdominal musculature
Figure 3:
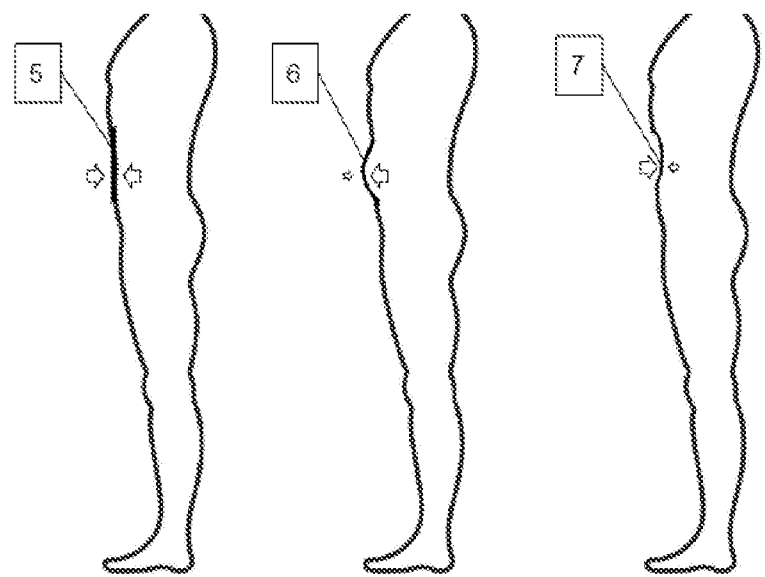
FIG. 3.—shows a side view of rectus abdominis muscle contraction positions
Figure 4:
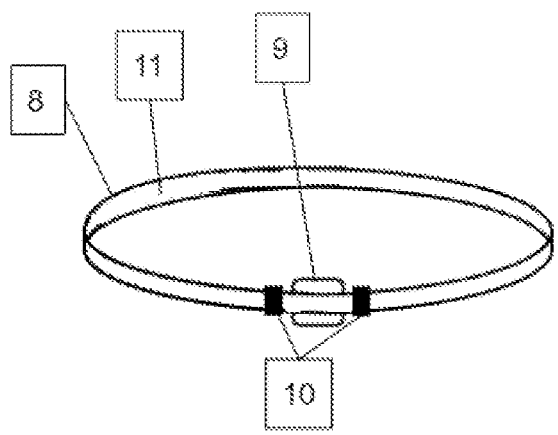
FIG. 4.—shows a front isometric view of a belt device that is to apply inward pressure to abdomen FIG. 5.—shows a side view of a belt device that is to apply inward pressure to abdomen FIG. 6.—shows an in situ side view of a belt device that is to apply inward pressure to abdomen FIG. 7.—shows an in situ rear view of a belt device that is to apply inward pressure to abdomen FIG. 8.—shows dimensional definitions of abdominal member in relation to wearer
Figure 5:
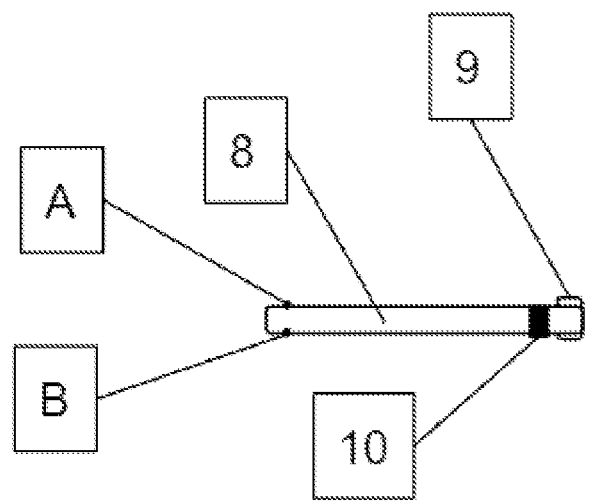
Figure 6:
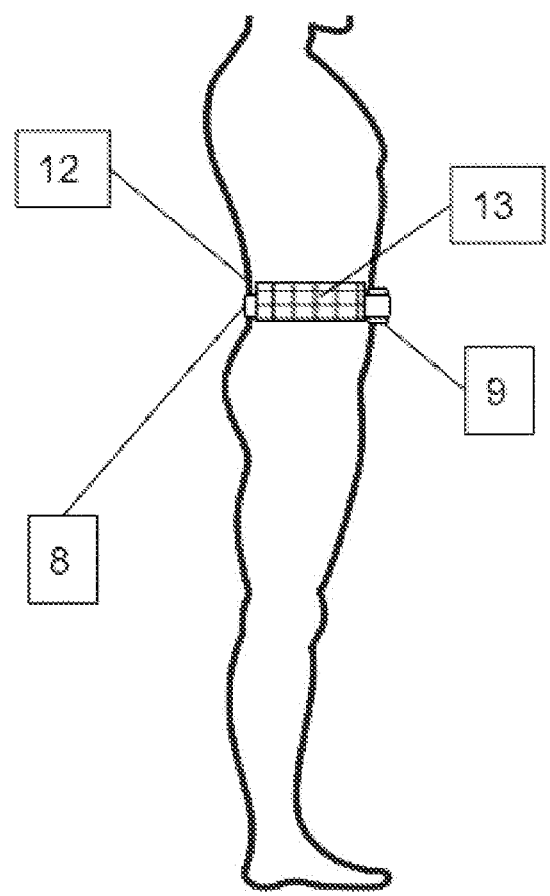
Figure 7:
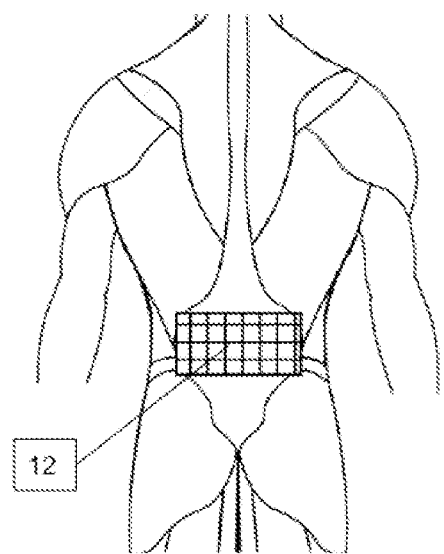
Figure 8:
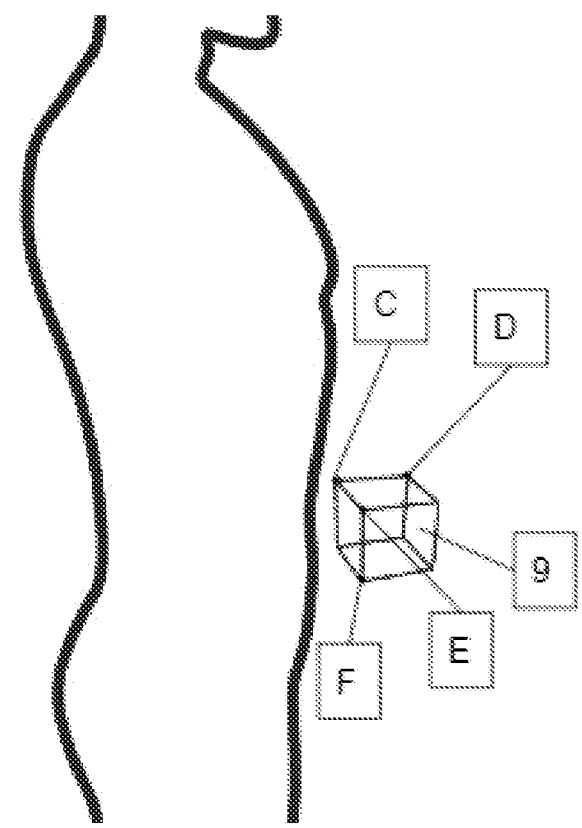

Referring now in detail to the drawings for the purpose of illustrating preferred embodiments of the present invention refers to the labels on FIGS. 1, 2, 3, 4, 5, 6, 7 and 8.

In a first embodiment, the following method causes abdominal bracing and improvement of pelvic, neck and back posture by providing focus on a specific area of the abdominal muscles at the front of the body and not on the sides, back muscles or spine of the user. The user is instructed in the following method:

Step 1—Normal Posture. Begin in your relaxed, normal standing position and posture without contraction or tension in the abdominal muscles.

Step 2—Activation Point Location. Locate a point mid-sagittal on your abdominis rectus muscle (1) inferior to the umbilicus (2)—refer to the allowed activation area (3). (Do not locate a point above the umbilicus (2), as this will cause excessive curvature in the lower back.).

Step 3—Inward Pressure. Apply deep inward pressure on the point located in the activation point location step, while the abdominal muscles are relaxed. Do not contract abdominal muscles during this step, allow the inward pressure on the single point (4) to push your abdominal muscles inward. Do not release the inward pressure.

Step 4—Muscle Contraction. Do not release the inward pressure. With a long breath out, actively contract only the part of your rectus abdominis muscle (1) that is receiving deep inward pressure (4) to push outward against the inward pressure. Continued muscle contraction of the small area of the rectus abdominis outward combined with continued inward pressure will ensure that the rectus abdominis muscle is braced in a vertical position (5), not bulging outward (6), and not hollowed inward (7).

Step 5—Activation of Posture Correcting Muscles. Continue to use only the contacted area (3) of your rectus abdominis muscle (1) to push against the continued inward pressure. Continued, balanced outward abdominal muscle push against inward pressure (5) causes antagonistic muscle pairs on the anterior and posterior of your body (including lower back, upper back, chest, shoulders, neck and abdominal bracing muscles) to correctly adjust the posture of your pelvis, back, shoulders and neck.

Step 6—Corrected posture. Hold your abdominal muscles in this position, and take several steps forward to allow all your pelvic, abdominal, back, chest, shoulder and neck muscles to adjust themselves to your new muscle configuration.

In a second embodiment, the invention describes a belt worn by the user around the lower abdomen capable of applying continuous, localized, deep pressure to a single point (4) mid-sagittal on the wearer's abdominis rectus (1) muscle inferior to the umbilicus (2). The belt described in this embodiment comprises a narrow, adjustable strap formed by an inextensible material (8); an abdominal contact member (9) comprising a thick rectangular solid block of a low compressibility material; and clasp mechanisms (10); capable of adjusting the length of said belt (8).

The abdominal contact member (9) is attached to the interior surface (11) of the belt (8) by means of any suitable method of attachment such as hook and loop or a pocket of fabric attached to the interior surface of the belt. The belt (8) is made of a resilient material such as, but not limited to, nylon or polypropylene. The belt width (dimension between labeled points A and B) is narrow so as to touch only a small area on the sides and front of the wearer's abdomen (13); the lumbar region (12) contact surface of the belt (8) may be wider than the lengths of the belt (8) material which touch the sides and front of the abdominal area (13) for the purposes of comfort of the wearer. The abdominal contact member (9) is of small contact area so as to apply deep localized pressure to a single point (4) mid-sagittal on the wearer's abdominis rectus (1) muscle inferior to the umbilicus (2). The abdominal contact member (9) is made of a resilient material which will not easily compress such as, but not limited to, a dense foam.

The combination of a small contact area, roughly cubic shaped abdominal contact member (9) and narrow width belt (8) ensures the greatest localized pressure that the wearer feels is only at the site on the abdomen where the abdominal contact member (9) is placed. The clasps (10) capable of tightening said belt (8) may be located at any point along the resilient belt (8). The clasps (10) are located to the lateral sides of the abdominal contact member (9). The clasps (10) are not limited to any specific type of belt or strap tightening device. Tightening of the belt (8) may be accomplished with only a single clasp (10). The abdominal contact member (9) has a minimum thickness (dimension between labeled points C and D) of 35 mm in order to produce the desired result as described in the method of the first embodiment. The abdominal contact member width (dimension between labeled points C and E) and abdominal contact member height (dimension between labeled points E and F) of the surface of the member which contacts the user can be varied by those skilled in the art. The foregoing is considered as illustrative only of the principles of the invention.

Although the present invention has been described in detail in regard to the certain embodiments and drawings thereof, it should be apparent to those skilled in the art that suitable modifications and equivalents may be resorted to without departing from the spirit and scope of the invention.

The invention claimed is:

1. An abdominal bracing and posture correction device comprising: an adjustable belt; at least one buckle and clasp to tighten said adjustable belt; and a contact member configured to apply pressure to a small area of a rectus abdominis muscle, mid-sagittal and below an umbilicus when the adjustable belt is in situ so as to provide inward pressure to said small area; wherein the contact member is configured to apply deep inward pressure on the small area for contraction at the small area and relaxation at remaining areas of the rectus abdominis muscle; wherein a material of which the contact member is formed is of low compressibility; wherein a location of the contact member on the adjustable belt is at an interior surface; wherein a width of the adjustable belt for contacting a torso of a wearer consists of a dimension not greater than 52 mm at anterior and lateral regions, and not greater than 300 mm at a lumber region; wherein dimensions of the contact member consists of a minimum thickness of 35 mm, a minimum width of 25 mm, and a maximum width of 77 mm.

2. The abdominal bracing and posture correction device of claim 1, wherein the at least one buckle and clasp comprises a single buckle and clasp.

3. The abdominal bracing and posture correction device of claim 1, wherein the at least one buckle and clasp comprises a plurality of buckles and clasps.

4. The abdominal bracing and posture correction device of claim 1, wherein the adjustable belt is formed from flexible but inextensible material.

* * * * *